US007789871B1

(12) United States Patent
Yandell

(10) Patent No.: US 7,789,871 B1
(45) Date of Patent: *Sep. 7, 2010

(54) VIAL ASSEMBLY AND METHOD FOR REDUCING NOSOCOMIAL INFECTIONS

(76) Inventor: Marion E. Yandell, 1439 Finn Hall Rd., Port Angeles, WA (US) 98362

( * ) Notice: Subject to any disclaimer, the term of this patent is extended or adjusted under 35 U.S.C. 154(b) by 0 days.

This patent is subject to a terminal disclaimer.

(21) Appl. No.: 12/620,439

(22) Filed: Nov. 17, 2009

Related U.S. Application Data

(63) Continuation-in-part of application No. 11/857,670, filed on Sep. 19, 2007, now Pat. No. 7,618,408.

(60) Provisional application No. 60/826,287, filed on Sep. 20, 2006, provisional application No. 60/890,134, filed on Feb. 15, 2007.

(51) Int. Cl.
*A61B 19/00* (2006.01)

(52) U.S. Cl. ........................ 604/414; 604/403; 604/411

(58) Field of Classification Search ................. 604/403, 604/405, 406, 411–416
See application file for complete search history.

(56) References Cited

U.S. PATENT DOCUMENTS

| | | | |
|---|---|---|---|
| 3,527,215 | A | 9/1970 | DeWitt |
| 3,584,770 | A | 6/1971 | Taylor |
| 4,265,364 | A | 5/1981 | Baba |
| 4,386,929 | A | 6/1983 | Peery et al. |
| 4,673,404 | A | 6/1987 | Gustavsson |
| 5,329,294 | A | 7/1994 | Ontowar et al. |
| 5,400,573 | A | 3/1995 | Crystal et al. |
| 5,488,400 | A | 1/1996 | Crystal et al. |
| RE35,187 | E | 3/1996 | Gortz |
| 5,572,852 | A | 11/1996 | Crystal et al. |
| 5,662,734 | A | 9/1997 | Crystal |
| 5,685,866 | A | 11/1997 | Lopez |
| 5,686,948 | A | 11/1997 | Crystal et al. |
| 5,695,466 | A | 12/1997 | Lopez |
| RE36,410 | E | 11/1999 | Meshberg |
| 6,196,669 | B1 | 3/2001 | Harvey et al. |
| 6,258,062 | B1 | 7/2001 | Thielen et al. |
| 6,290,332 | B1 | 9/2001 | Crystal et al. |
| 6,361,230 | B1 | 3/2002 | Crystal et al. |
| 6,398,031 | B1 | 6/2002 | Freeza |
| 6,478,492 | B1 | 11/2002 | Crystal et al. |
| 6,572,592 | B1 | 6/2003 | Lopez |
| 6,669,673 | B2 | 12/2003 | Lopez |
| 6,761,286 | B2 | 7/2004 | Py et al. |
| 6,883,907 | B2 | 4/2005 | Martinez |
| 6,966,639 | B2 | 11/2005 | Martinez-Pacheco |
| 7,000,806 | B2 | 2/2006 | Py et al. |
| 2006/0264845 | A1 | 11/2006 | Lopez |
| 2006/0264891 | A1 | 11/2006 | Lopez |
| 2006/0264892 | A1 | 11/2006 | Lopez |
| 2007/0244456 | A1 | 10/2007 | Fangrow |

*Primary Examiner*—Leslie R Deak
(74) *Attorney, Agent, or Firm*—Jacques M. Dulin, Esq.; Innovation Law Group, Ltd.

(57) ABSTRACT

Vacuum break vial assembly and method for reducing the incidence of nosocomial infections, comprising a vial stopper having a 2-part withdrawn-fluid volume compensation assembly having a barbed vent element that secures an apertured needle sheath, a bladder-retainer tube and an expandable/unfoldable bladder. The vial has an aluminum cap holding a plastic flip-off top that removes a central portion of the cap to permit access by hypodermic needle through the stopper into the needle sheath. No pre-pressurization of the vial by ambient contaminated air via the hypodermic can occur. Rather, the needle is inserted in the vial through the stopper and the medicinal fluid withdrawn. Air is inlet into the separate bladder which expands to permit withdrawal of fluid into the hypodermic without vacuum lock. No air having pathogen vectors is introduced into the vial medicinal fluid as the bladder isolates volume-compensating air from the medicinal fluid. Plural embodiments are shown.

18 Claims, 6 Drawing Sheets

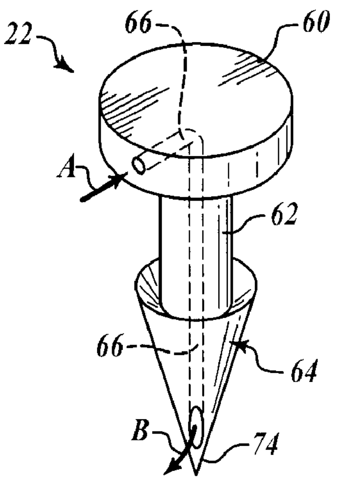
FIG. 1A
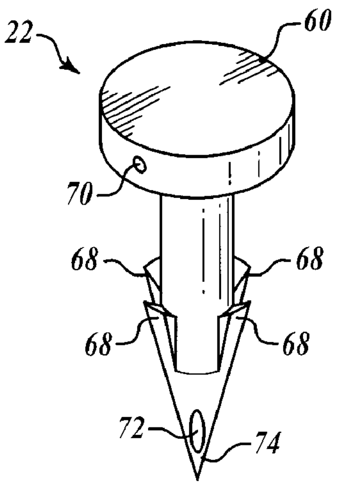
FIG. 1B
FIG. 1C
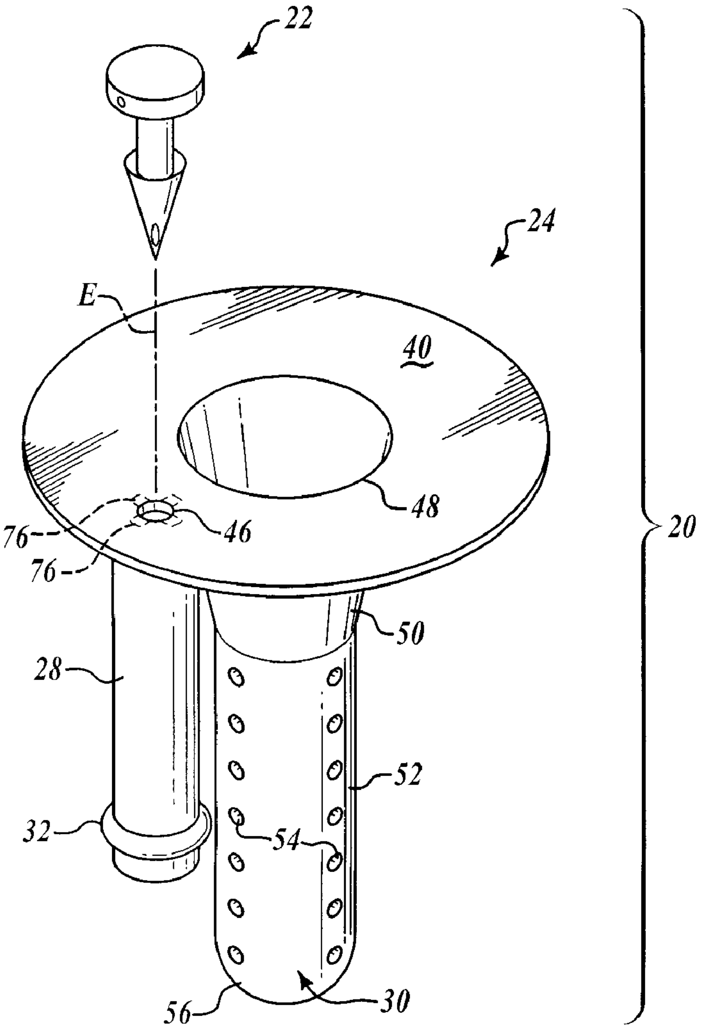

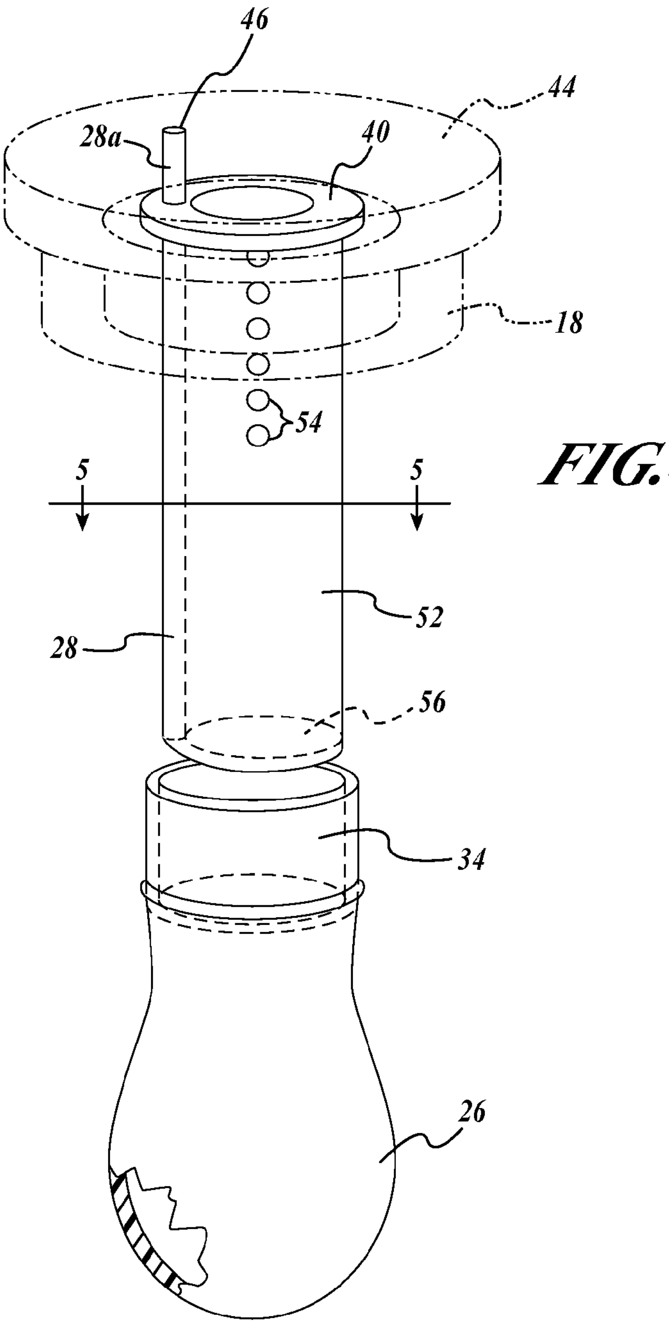
FIG. 4
FIG. 5
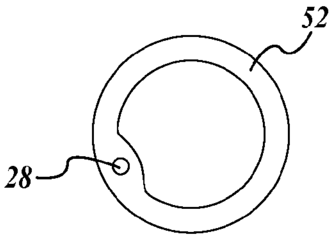

VIAL ASSEMBLY AND METHOD FOR REDUCING NOSOCOMIAL INFECTIONS

CROSS-REFERENCE TO RELATED CASES

This is a CIP of U.S. appplication Ser. No. 11,857,670 filed Sep. 19, 2007 by the same inventor, scheduled to Issue as U.S. Pat. No. 7,618,408B2 on Nov. 17, 2009, which in turn is the Regular US Patent Application corresponding to two Provisional Applications of the same inventor: Ser. No. 60/826,287, filed Sep. 20, 2006, entitled Vial Assembly for Reducing Nosocomial Infections, and Ser. No. 60/890,134, filed Feb. 15, 2007, entitled Vial Assembly for Reducing Nosocomial Infections—II, the benefit of the filing dates of each of which is claimed under 35 USC 119 and 120, and the disclosures of which are hereby incorporated by reference.

FIELD

The invention relates to the field of reducing the incidence of generation and transmission of nosocomial infections, commonly introduced into medicinal injection vials via hypodermic needles followed by transmission upon withdrawal of the infected vial solution and injection into the patients, and more particularly to a novel vacuum break system comprising a vial stopper assembly that includes a needle sheath and withdrawn fluid compensation assembly mounted in the elastomeric plug of the vial.

BACKGROUND

Nosocomial infections are any infections generated in the hospital. Many of these are a result of treatment by hypodermic-delivered injectable medications. These infections are secondary to the patient's original condition. According to the Centers for Disease Control and Prevention, in the United States alone, it has been estimated that as many as one hospital patient in ten (or 2 million patients a year) acquires a nosocomial infection. Estimates of the annual cost range from $4.5 billion to $11 billion and up. Nosocomial infections contributed to 88,000 deaths in the US in 1995. Nosocomial infections are even more alarming in the 21$^{st}$ century as antibiotic resistance spreads. Warning signs in some hospitals state "For every minute you are in a hospital, you will pick up from 8 to 15 bacteria on your hands."

One of the most common vectors for transmission of viral and microbial infections is airborne. One mode by which airborne microbes infect patients is via ambient-microbe-laden air introduced into medicinal vials by nurses giving shots.

In current practice, ambient air is drawn into hypodermic needles and then injected into vials to pressurize the vials so as to prevent vacuum lock. This air is laden with airborne microbes, and they are then injected into the bottle, mix with the medicinal fluid where they may incubate over extended periods before the next use. They are then, or later, withdrawn into the hypodermic with the medicinal fluid and injected directly, sub-dermally into the patient, often directly into the blood-stream or intra-muscularly. In addition, special medical fluids are introduced by hypodermics into IV lines (typically by Y-tube connectors or into the bags themselves), thus contaminating the IV fluid.

The reason for injecting ambient air into the vial is to overcome the vacuum-lock—that is, withdrawing fluid from the vial creates a vacuum so strong that the hypodermic cannot be filled. While open medicine bottles have been abandoned as unsanitary for over 50 years, there has been little, if any, recognition of the introduction, at the time of filling of the hypodermic, of microbes in the ambient air introduced into closed vials via the step of first pressurizing the vial with the hypodermic full of ambient air.

Soft, pliable plastic blood bags and saline bags are used for gravity feed of fluids to bed-bound patients. No vacuum lock occurs, as the bags collapse under external air pressure. In addition such bags are always elevated so the fluid is gravity fed. In addition the fluid is usually introduced into a vein, where the moving blood accepts the added fluid. For uphill drip systems, Peery et al discloses in U.S. Pat. No. 4,386,929 an elastically pressurized medicinal fluid container. In contrast, in sub-dermal injection by hypodermic, the injected fluid is forced into muscle under considerable pressure to form its own bolus.

Vacuum lock issues have been addressed in far different arts—including ink jet cartridges, baby bottle nipples, wine bottle stoppers and the like. An example of internal bladders plus bubble vents to address "over driving" of ink cartridges and fade-out during printing caused by vacuum lock issues in the ink jet cartridge field is U.S. Pat. No. 5,686,948 in Class 347/85 (also see 347/86, 87 and Class 141/2, 18 and 19). However, there the issue is different: There, air can be inlet through the fluid ink by the bubble vent 53, while the "lungs" 44, 46 (bladder and spring) function to provide back pressure and to compensate for the relatively constant rate of withdrawal during printing. Inlet air fills the void left by used ink.

In contrast, withdrawal from a medicine vial is in large, intermittent aliquots—something the ink jet cartridge is not designed to handle. Further, air in contact with medicinal fluid would contaminate it.

Some hospital and clinical protocols call for filling hypodermics from vials, especially hazardous drugs or biologics, under conditions that protect health care workers and patients, including hoods or other areas with ISO Class 5 environment with protective engineering controls and aseptic practices. However, it has been determined that in a USP 797 standard laminar flow hood there are still on the order of 20,000 contaminants per cubic foot of air.

There is an urgent need in the art for solving the problems specific to transmission of nosocomial infections via introduction of microbes into medicinal vials during pressurization by hypodermic needles.

THE INVENTION

The invention is directed to a vacuum break vial assembly and method for reducing the incidence of generation and transmission of nosocomial infections, comprising a vial stopper having a 2-part withdrawn-fluid volume compensation assembly, which includes a barbed vent element that secures an apertured needle sheath, a bladder-retainer tube and an expandable or unfoldable bladder. The vial has an aluminum top cap crimped around the lip of the vial mouth that carries a plastic flip-off top. When removed that top carries away a central portion of the cap revealing a target ring molded into the top of the elastomeric vial stopper. The ring provides a target for insertion of a hypodermic needle into the needle sheath. The sheath protects the bladder from piercing by needle, and includes small lateral holes so that the needle can withdraw medicinal fluid from the vial.

In present practice the vial has to be pre-pressurized by drawing air into the hypodermic and injecting that into the vial before withdrawing fluid. In the inventive system method, no pre-pressurization of the vial with air injected by the hypodermic is needed. Rather, the needle is un-capped and directly inserted in the vial through the stopper and the medicinal fluid withdrawn. Air enters into the separate bladder via the vent barb element, and the bladder expands to permit withdrawal of fluid into the hypodermic without vacuum lock. No ambient air having pathogen vectors is introduced into the vial medicinal fluid, as the bladder isolates volume-compensating air from the medicinal fluid.

In each of the several embodiments of the inventive vial assembly having the vacuum-break feature which permits withdrawal of medicinal fluid from the vial without prior pressure-zation, the medicinal fluid is kept separate from the air, thus eliminating contamination and the need for the USP 797 standards under ISO Class 5 environment and procedures. The isolation of the medicinal fluid from the air is necessary to fill the void in the vial left when fluid is removed and so that in fact the fluid can be removed. Without volume compensation, vacuum lock would occur.

In all embodiments, pre-pressurization of the vial by hypodermic is both unnecessary and to be avoided. The hypodermic can be filled with the bottle or vial upright or in the standard, inverted-fill position. In all embodiments the principles are the same, an expanding bladder, expanding bellows or sliding diaphragm moves in the vial as medicinal fluid is withdrawn to compensate for the volume of fluid withdrawn. No vacuum lock occurs as the filled volume is reduced by withdrawal of fluid, and no contaminated air comes into contact with the medicinal fluid.

The first, preferred embodiment employs a special needle sheath assembly mounted centrally in a planar annulus or ring that is gripped by the depending collar of the vial stopper. The central opening communicates with a conical funnel, the bottom of which communicates with a perforated sleeve. The bottom end of the sleeve is closed and of thickness to prevent piercing by the needle. This needle sheath permits introduction of the needle through the elastomeric plug, but the needle will not pierce the bladder as the apertures in the sleeve are laterally oriented and the lower end is robust enough to prevent being pierced by the sharp tip of the needle. In addition, the preferred configuration of the needle sheath includes a sleeve long enough to provide free space between the end of the needle and the closed end of the sheath even when the hypodermic is pushed deeply into the vial, even far enough that the ferrule of the needle contacts the plug target ring.

The bladder is initially collapsed when the inventive vacuum-break assembly, as mounted in the stopper is fitted in the vial filled with medicinal fluid. The top of the vial is fitted with a special stopper assembly comprising a plug body, a needle sheath and a sealing membrane through which a hypodermic needle is inserted. The rigid needle sheath has side-wall perforations that permit medicinal fluid to flow into the needle, but stops the needle from penetrating deeply into the vial, where it might otherwise puncture the bladder as it expands. As medicinal fluid is withdrawn from the vial, air enters the bladder through the perforated bottom cap so the bladder or bellows expands to compensate for the volume of the fluid withdrawn. Thus, as the vial is emptied of medicine, the bladder or bellows will inflate or expand to replace it. By the inventive vial assembly, it is no longer necessary to pre-pressurize, at each withdrawal, the vial by air injected with the hypodermic.

In the second embodiment employs a vial with side air vents is fitted with an internal plastic or elastomeric bag. The expandable bag is filled with medicinal fluid, and sealed to the cap assembly. The elastomeric stopper includes a needle sheath but does not include the barbed vent and bladder retaining tube. The bladder may be a thin plastic, medical grade material that collapses as the air enters through the side air vents. The bladder may also be a corrugated construction that collapses as the fluid is withdrawn. In this embodiment the bladder may be fitted with a flat, more robust, relatively rigid bottom plate to permit more even and uniform collapse of the bag, and a coil spring may be provide there-beneath to urge the bladder to a collapsed condition by positive pressure. The needle sheath prevents the bladder from being punctured by a hypodermic needle. Air enters through the side air vents to fill the void created in the glass vial as the plastic bag is depleted of medicinal fluid.

The third embodiment employs a balloon-type bladder located inside a standard vial fitted with the inventive stopper fitted with the needle sheath (but no barbed vent). An air tube runs through an edge or collar member of the stopper, and into the expandable bladder, sealed around the tube. The lower half of the tube, which is inside the balloon, is perforated, so that air entering through the top of the vent tube exiting stopper passes down the tube into the balloon permitting it to expand, as medicinal fluid is removed from the vial.

In another embodiment, an air lumen is provided in the side wall of the needle sheath, which is generally tubular, and may include a flange at the top to engage and assist in being secured by the vial stopper elastomeric material. The lumen continues above the top edge of the needle sheath tube or flange in the form of a small tube. This airway tube/lumen is just long enough to extend to the top surface of the elastomeric stopper. The bottom of the needle sheath tube is closed, and a short sleeve, to which the bladder is secured, sealingly slips over or is threaded onto the bottom of the needle sheath tubing. Thus the lumen communicates with the bladder at the lower end and to the atmosphere via the short tubing at the top. This embodiment thus provides a single axial needle sheath/bladder geometry, as compared to the side-by-side geometry of other embodiments, above.

These several embodiments are offered as examples of different combinations of the two inventive features which solve the problem in the art—that is, needle sheath stopper assemblies (with or without a barbed vent element) and expandable bladders or bellows which isolate the medicinal fluid from the air so that no vacuum seal develops as the medicinal fluid is withdrawn from the vial.

BRIEF DESCRIPTION OF THE DRAWINGS

The invention is described in detail by reference to the drawings, in which.

a the second embodiment having a bellows with needle shield in place of a needle sheath, showing a vial containing medicinal fluid, with an air inlet through the bottom of the vial to allow air to flow into the sealed bellows-type expandable bladder.

Figure 1D:
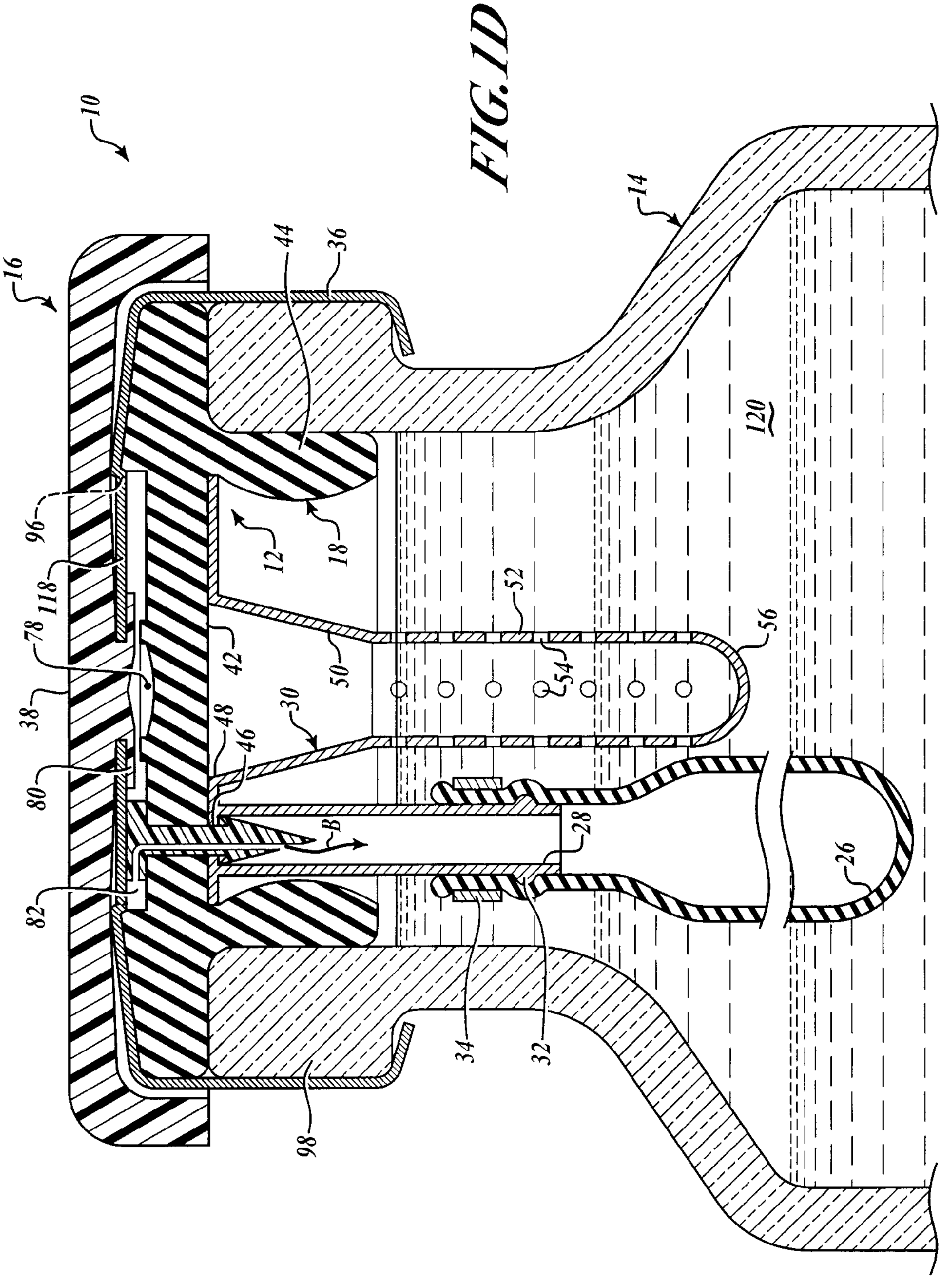
FIG. 1D is a cross-section view of the inventive vacuum break assembly inserted in the neck of a standard medicinal vial, complete with cap, flip top and expandable air bag mounted on the bag retaining tube.
Figure 1E:
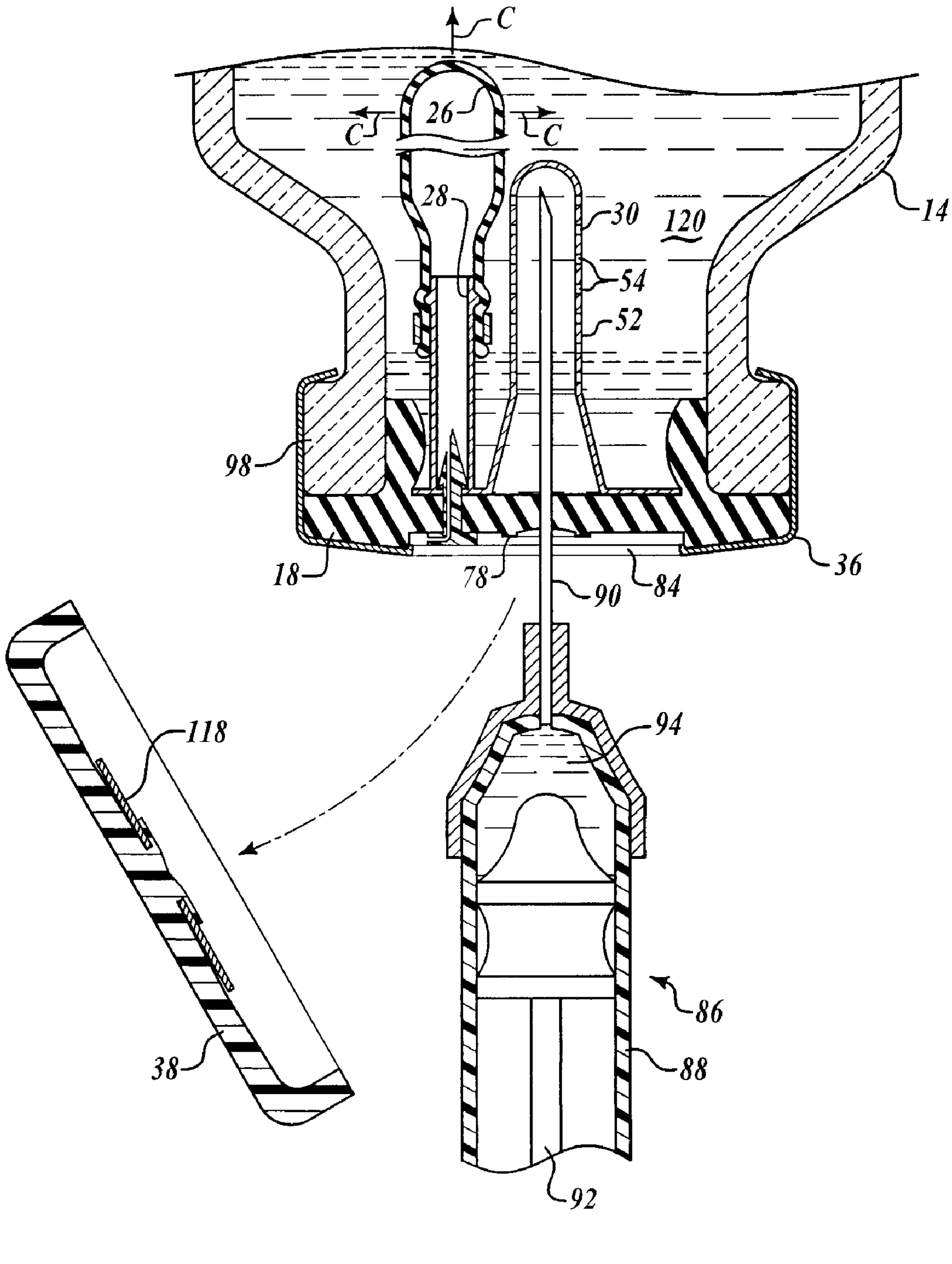
FIG. 1A is an isometric view of the barbed vent element in a first embodiment implementation.
FIG. 1B is an isometric view of a second embodiment of the barbed vent element showing the flexible engaging barbs.
FIG. 1C is an isometric, partly exploded, view of the needle sheath and volume compensation assembly (without expandable air bag) showing the alignment for insertion of the vent element of FIG. 1A.
Figure 2A:
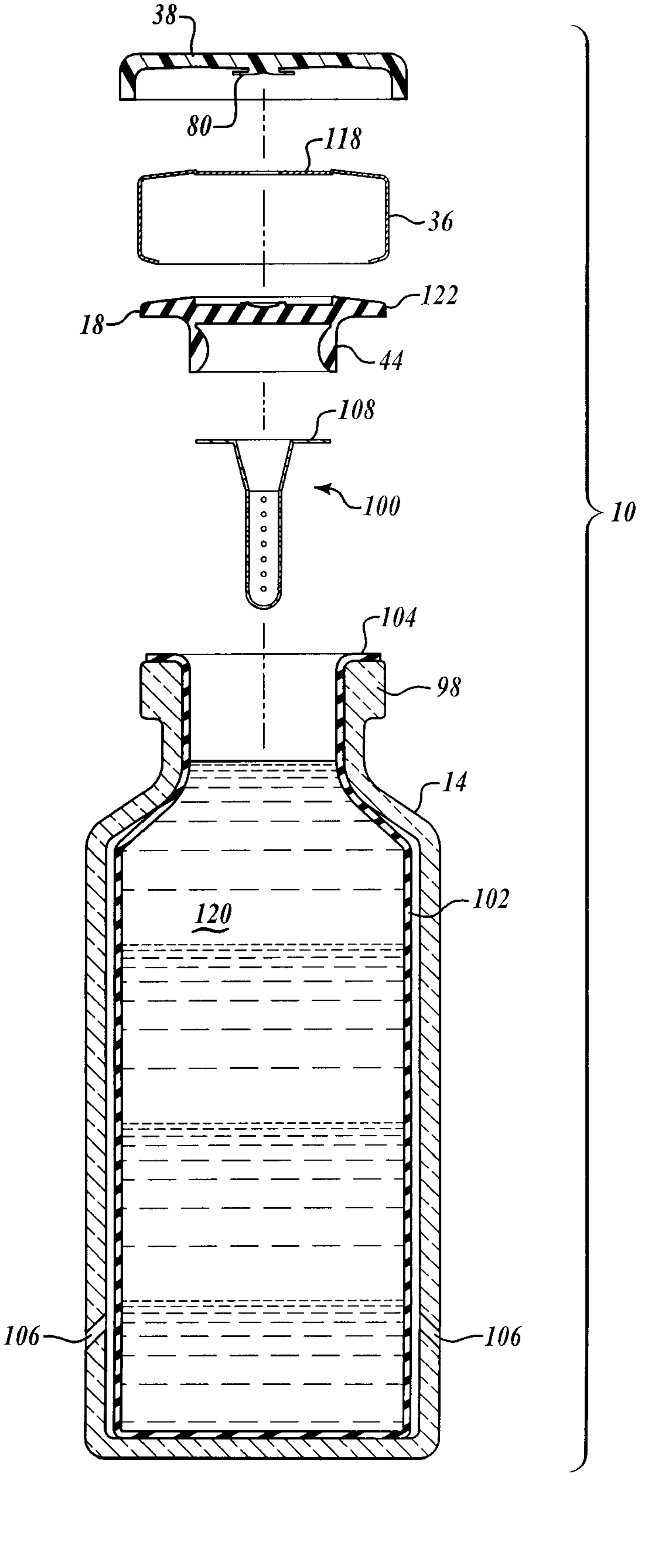
Figure 2B:
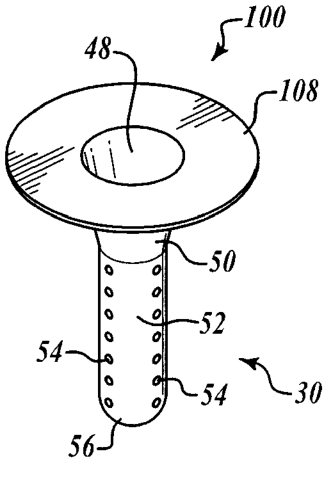
Figure 3:
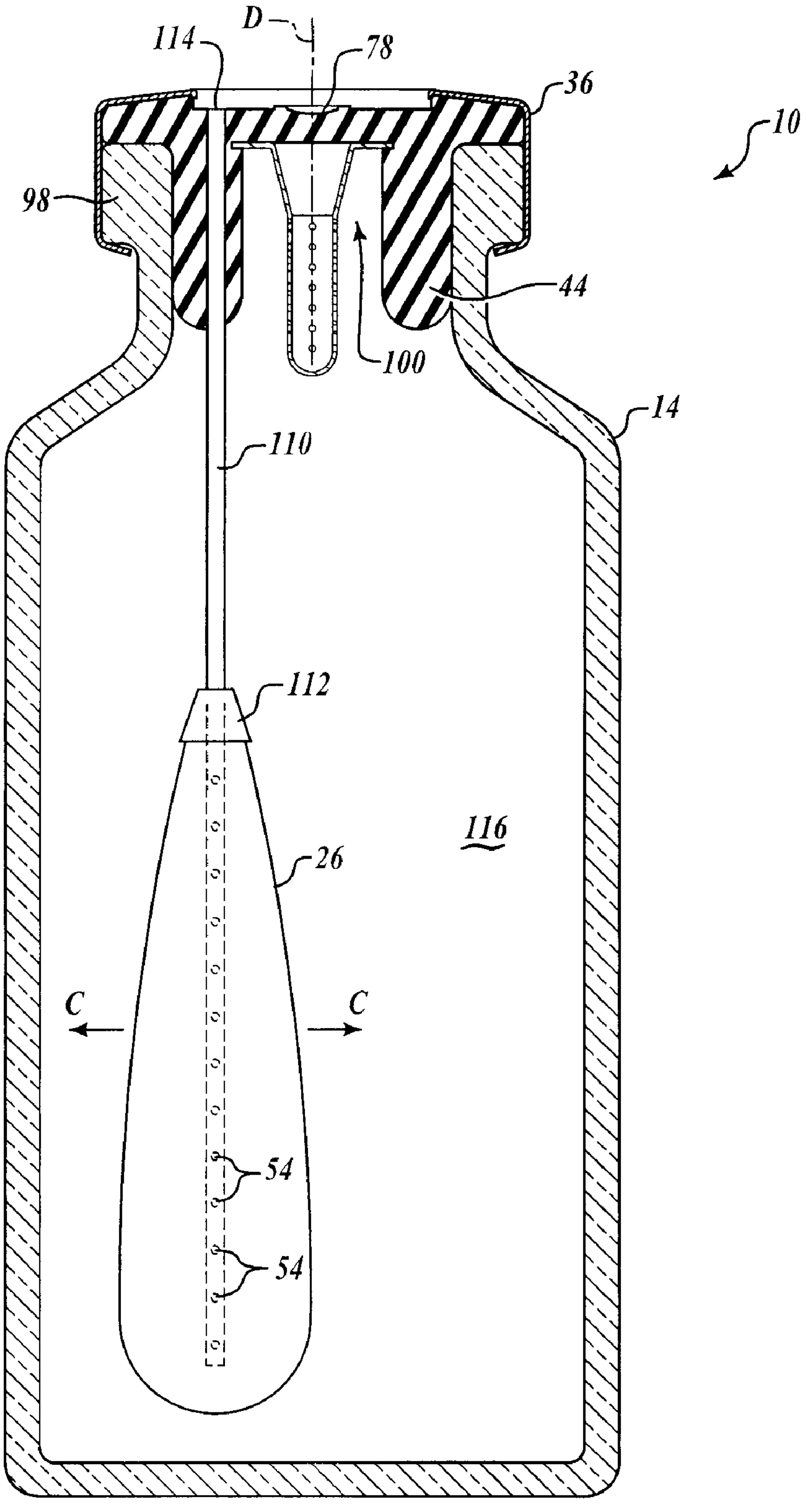

FIG. 1E is a cross-section view of the method of withdrawing an aliquot of medicinal fluid from the vial after the flip top has been removed and the hypodermic needle inserted through the stopper into the needle sheath but without having to pre-pressurize the vial and not contaminating the medicinal fluid in the vial;

FIG. 2A is an exploded cross-section view of a third embodiment of the inventive vacuum break system showing a medicine-filled, collapsible bladder inside a glass vial having side wall air inlets and a needle sheath mounted in the stopper;

FIG. 2B is an isometric of the needle sheath for the assembly of FIG. 2A;

FIG. 3 is a cross-section view of a fourth embodiment of the inventive vacuum break assembly showing a vial having a stopper with needle sheath fitted thereto, and an offset air inlet tube with a balloon-type expansion bladder inside the vial;

FIG. 4 is an isometric view of a fifth embodiment of the inventive vacuum break assembly showing an axially in-line geometry of the bladder below the end of the needle sheath which communicates with the exterior atmosphere via a lumen in the side wall; and FIG. 5 is a section view through line 5-5 of FIG. 4 showing the lumen in the side wall of the needle sheat tube.

DETAILED DESCRIPTION OF THE INVENTION, INCLUDING THE BEST MODE

The following detailed description illustrates the invention by way of example, not by way of limitation of the scope, equivalents or principles of the invention. This description will clearly enable one skilled in the art to make and use the invention, and describes several embodiments, adaptations, variations, alternatives and uses of the invention, including what is presently believed to be the best modes of carrying out the invention.

In this regard, the invention is illustrated in the several figures, and is of sufficient complexity that the many parts, interrelationships, and sub-combinations thereof simply cannot be fully illustrated in a single patent-type drawing. For clarity and conciseness, several of the drawings show in schematic, or omit, parts that are not essential in that drawing to a description of a particular feature, aspect or principle of the invention being disclosed. Thus, the best mode embodiment of one feature may be shown in one drawing, and the best mode of another feature will be called out in another drawing.

All publications, patents and applications cited in this specification are herein incorporated by reference as if each individual publication, patent or application had been expressly stated to be incorporated by reference.

The views in the Figures and numbered parts permit one skilled in the art of medicinal vial design and manufacture, by reference to the attached parts list, to easily understand the materials, mode of construction and assembly, and the method of use.

FIGS. 1A-1E should be considered together as they show the individual parts (FIGS. 1A-1C), the assembly (FIGS. 1C, 1D) and the use (FIG. 1E) of the inventive vacuum-break vial assembly 10 useful for reducing the incidence of airborne nosocomial infection vectors and airborne contaminants. The inventive vacuum-break vial assembly 10 comprises a stopper assembly 12 (FIG. 10) mounted and secured in the neck of a standard medicinal vial by an aluminum cap 14, the bottom edge of which is rolled around the bead 98 of the mouth of the vial 14. The aluminum cap also includes a circular break-away top section 118 defined by perforations 96, which section is removed by thumbing-off the "Flip-Off" cover 38. FIG. 10 shows the assembly as received by the medical professional, ready for use, and FIG. 1E shows the cover 38 flipped off with the circular section 118 removed, having been retained by the connecting tab or mushroom 80. This action reveals the needle access hole 84 (FIG. 1E) of the cap 36, defined by the removal of the circular break-away section 118.

The vial 14 may be any standard or custom glass or plastic vial suitable for medical fluid use, and the cap, break-away disc and flip-off cover may be a standard assembly of the type that is currently available in the industry. Thus, the inventive vacuum-break assembly does not involve any re-tooling for the sterilizing, filling, closure and capping of vials.

In more detail, the stopper assembly 12 of FIGS. 1D and 1E comprises a standard elastomeric (such as neoprene) stopper 18 fitted with a 2-part volume compensation assembly 20, shown in FIG. 1C exploded, and shown in FIG. 10 and FIG. 1E assembled and in use, respecttively. The volume compensation assembly 20 comprises a barbed vent element 22 and a needle sheath and bladder container assembly 24, seen in isometric in FIG. 1C. These parts are preferably made of stainless steel, but in the alternative, one or both may be made of a strong, rigid, medical grade plastic that may be sterilizable, e.g., by steam, ethylene oxide, glutaraldehyde, or any standard sterilization technique. As seen in FIG. 1E, the amount 94 of medicinal fluid 120 withdrawn from the vial 14 by retracting the plunger 92 in the bore 88 of the hypodermic 86 is compensated-for the by the expansion of the bladder, bag or balloon 26, the expansion being shown by the Arrows C. Note that FIG. 1C does not show the bladder 26, but that element of the inventive system is best seen in FIGS. 1D and 1E, fitted on and secured to the bladder retaining tube 28 (see FIGS. 1C-1E). The bladder is retained on the retaining tube 28 by one or more ridge(s), flange(s) or lip(s) 32, and an optional metal or elastomeric band 34 (best seen in FIG. 1D). An exemplary metal band material may be crimpable aluminum or stainless steel.

As shown, but only by way of example, the bladder may be an elastomeric balloon that expands in size by introduction of air via the barbed vent element 22 as fluid 94 is withdrawn by the hypodermic 86. In that example, the balloon should be easily expandable so that the balloon does not resist volume compensation. In another example, the bladder 26 may be a corrugated container that expands from a flattened condition (when the vial is full) to an expanded condition as the vial is emptied. In still another example, the balloon may be a folded or rolled-up tubular plastic bag that unfurls as the fluid is withdrawn from the vial.

FIGS. 1A and 1B show two exemplary embodiments of the barbed vent element 22. In a first embodiment of FIG. 1A, the barbed vent 22 comprises a flattened stud portion 60 to which is secured a stem portion 62, that terminates in a barb portion 64 that terminates in a sharp piercing point 74. A vent channel or passage 66 is provided internally of the barbed vent 22 extending from an inlet hole 70 in the stud side wall through the stem and terminating in outlet hole 72 adjacent the point 74 (see FIG. 1B). The inlet air is shown by Arrow A and the outlet air by Arrow B in FIG. 1A.

As seen in FIGS. 1C and 1D, the barbed vent element 22 secures the needle sheath and air bladder retainer assembly 24 to the underside 42 of the stopper collar 44 by application of force to the stud 60 so that the point 74 pierces the stopper neoprene, passes through the hole 46 in the annulus 40 of the needle sheath assembly 30. The barbs engage underside of the annulus adjacent hole 46, as best shown in FIG. 1D, compressing the parts together under tension. The bladder may be fitted on the tube 28 before or after the barb is pressed through the stopper top web. The resulting inventive vacuum-break assembly is thus wedged in the stopper collar 44 when the stopper 18 is inserted in the neck of the vial 14, typically after filling with medicinal fluid 120.

In FIG. 1A the barb is a continuous tapered flange around the shank. In FIG. 1B the ring is segmented to form a plurality of individual barbules 68. To assist in the insertion of the barb 22 via path Arrow E through the hole 46, the barb(s) may be thin and flexible, but strong, or the hole may include a plurality of slots or cuts 76. One of ordinary skill in this art can easily adjust dimensions to permit automated assembly with high yield. As assembled (best seen in FIGS. 1D and 1E), air can pass through the vent passage 66 from the space 82 which is open to atmosphere when the flip off cover is removed into the bladder 26. Thus, as the fluid is withdrawn the bladder expands, and no vacuum lock is formed, yet there is no contact of ambient air, containing as it does microbial and viral vectors, with the medicinal fluid. In short the inventive system prevents contamination during dosage use of the medicinal.

As seen in FIGS. 1B-1E, the needle sheath assembly 30 prevents puncture of the bladder 26 by the needle 90 of the hypodermic 86. The needle sheath assembly 30 comprises an annular ring 40 the central hole 48 of which joins the upper end of a conical funnel portion 50 the bottom end of which joins a tubular sleeve portion 52 that terminates in a rounded, non-perforatable end 56. The sleeve has a plurality of holes 54 which let the medicinal fluid pass into the needle sheath so that the needle 90 can withdraw fluid, as best seen in FIG. 1E. The closed end 56 is preferably thickened or re-enforced so that any unusually long or non-standard needles do not perforate the end. When the flip-off top 38 is removed, tearing away the cover disc 118 portion of the aluminum cap 36, a target ring 78 is revealed molded into the top surface of the neoprene stopper 18. That ring provides a target for the nurse to aim the needle 90. Note the conical funnel at its upper end is at least as wide as the diameter of the target ring 78. Thus, the needle enters the sheath 30 which protects the bladder 26. The nurse does not need to charge the vial with air; rather she simply flips off the cover 38, aims the needle at the center of the ring 78, inserts the needle through the neoprene into the sheath assembly 30 and withdraws the amount of fluid needed. The bladder expands as needed to prevent vacuum lock, and there is no contamination of the fluid with externally introduced air.

FIGS. 2A and 2B show a second embodiment of the inventive vacuum-break vial assembly 10, comprising a vial into which is fitted a full length bladder 102 that is made of a medical grade polymer to permit it being filled with a medicinal fluid 120. The bladder is configured with a neck to fit the vial neck, and a lip that generally conforms to the top lip 98 of the vial mouth. The bladder may also be a bellows configuration, or comprise an integral, relatively rigid diaphragm member at the bottom that moves upward as fluid is withdrawn. The vial also includes one or more small air vents 106 so that as fluid is withdrawn from the bladder, air can past into the space between the bladder and inner wall of the vial, permitting the bladder to contract or collapse to compensate for reduction in the volume of fluid in the vial. Recall that the vial is inverted from the orientation shown in this FIG. 2A, so that where the bottom includes a diaphragm member, it will slide down (up in the figure) to compensate evenly for fluid volume reduction.

This embodiment also includes a stopper 18 as before which grippingly retains a needle sheath 100 not having a bladder retaining tube. The upper annular planar member 108 is wedged into and retained by the collar 44 of the stopper. The stopper/needle sheath assembly is retained in the vial neck by an aluminum or stainless steel cap 36, having the same flip-off cover 38 with mushroom 80 for removing the tear-away disc 118. The needle sheath assembly 30/100 includes the same funnel portion 50, sleeve 52 with holes 54 and the robust end closure 56.

FIG. 3 shows a third embodiment of the inventive vacuum break vial assembly, in which the needle sheath 100 of FIG. 2A and FIG. 2B is fitted in a stopper with somewhat thickened collar. The cap 14 and flip-off top (not shown) are as in the other embodiments described above. An elongated vent tube 110 is inserted or cast into the wall of the stopper collar 44 as shown, and it terminates at its upper end in an air inlet 114 that provides air vial the holes 54 in the bottom section of the tube. A bladder collar 112 is fitted on the tube 110 and in turn a bladder 26 is secured by the collar. The bladder expansion is shown by Arrows C. The vial volume 116 is filled with medicinal before the stopper having the collapsed bladder wrapped around the air vent tube 110 and needle sheath assembly 100 is inserted into the vial neck. The Arrow D line shows the direction of insertion of the hypodermic in the center of the target ring 78.

It should be noted that the bladder/bellows/diaphragm may exert either neutral or positive force on the fluid in the vial depending on whether it is for air or fluid to compensate for volume change. That is, the bladder need not be a highly positive bellows or balloon exerting force to expel the fluid (e.g., in FIG. 2A). Rather, it may be neutral, so that the withdrawal of the fluid by hypodermic acts to create a momentary negative pressure in the vial and the bladder/bellows/balloon/diaphragm assembly expands in response to fill the volume formerly occupied by the withdrawn fluid. However, as needed or desired, the bellows/bladder/balloon/diaphragm may act like a compression spring, in that force is required to place it in a compressed state, and it provides positive pressure to assist in filling the hypodermic. The force to compress the bellows/bladder/diaphragm is provided by filling the vial with medicinal fluid under positive pressure, e.g., by fill pump. In addition, a spiral stainless steel spring may be used below the bellows, balloon or diaphragm 102 in FIG. 2A, the spring preferably being of large diameter to press upward on the periphery of the bellows or diaphragm, to assist it in overcoming any frictional resistance of the edge of the diaphragm that may be in contact with the inner side wall of the vial.

In a fifth, presently preferred embodiment, an air lumen 28 is provided in the side wall of the needle sheath 52, which is generally tubular, and may include a flange 40 at the top to engage and assist in being secured by the vial stopper elastomeric material 44. The lumen continues above the top edge of the needle sheath tube 52 or flange 40 in the form of a small tube 28*a*. This airway tube/lumen is just long enough to extend to the top surface of the elastomeric stopper providing an air inlet orifice 46. The bottom of the needle sheath tube is closed, e.g., by a plug 56, and a short sleeve or collar 34, to which the bladder 26 is secured, sealingly slips over or is threaded onto the bottom of the needle sheath tubing. Thus, the lumen 28 communicates with the bladder 26 at its lower end and to the atmosphere via the short tubing 28*a* at the top. This embodiment thus provides a single axial needle sheath/bladder geometry, as compared to the side-by-side geometry of other embodiments, above.

INDUSTRIAL APPLICABILITY

It is clear that the inventive medicinal vial assembly has wide applicability to the hospital, clinic and home health industries, namely to decrease the incidence of transmission of nosocomial infection by providing a vial assembly which prevents contaminated air from coming into contact with injectable medicinal fluids.

It should be understood that various modifications within the scope of this invention can be made by one of ordinary skill in the art without departing from the spirit thereof and without undue experimentation. For example, as long as the air and medicinal fluids are kept separate, the actual method by which air is introduced to fill the void created as medicinal fluid is removed may be widely varied by the use of different vial shapes, a variety of bladder and/or diaphragm designs and materials, and with the addition of various aids in addition to the needle sheath and aiming funnel. The barbed vent element may have a grooved side wall to provide an air passage rather than a passage in the body, and the air passage or groove need not bend at right angles in the stud, but may extend straight to the top of the stud. Although the needle sheath annular flange is shown gripped by the stopper collar in association with the interior surface of the stopper, it should be understood that the flange may be molded into the horizontal transverse web of the stopper central of the collar, so that it is effectively embedded into the stopper. The side vent(s) of FIG. 2A may be covered during storage or shipping with a security/protective tape that is removed just prior to use. This invention is therefore to be defined by the scope of the appended claims as broadly as the prior art will permit, and in view of the specification if need be, including a full range of current and future equivalents thereof.

The invention claimed is:

1. A medicinal vial vacuum break assembly for reducing the incidence and propagation of nosocomial infections resulting from airborne pathogen vectors or airborne contaminants introduced into medicinal fluids contained in said vial by pre-pressurization with ambient air injected by a hypodermic needle into said vial in the process of withdrawing a dose aliquot of fluid from the interior of said vial, comprising in operative combination:

a) an elastomeric stopper configured to fit in a neck of said vial, said stopper having an exterior surface and an interior surface, and a central web portion defined between said surfaces;

b) a needle sheath secured in association with said stopper, said needle sheath having a sleeve portion projecting into said vial, said sleeve having perforations to permit said medicinal fluid to be accessed by said hypodermic needle when introduced into said vial through said stopper web;

c) a bladder disposed in association with said vial to compensate for change in volume of medicinal fluid in said vial as said medicinal fluid is withdrawn from said vial, said bladder isolating external air for volume compensation from said medicinal fluid so that said vial does not have to be pre-pressurized to prevent vacuum lock; and d) an ambient air vent communicating with said bladder to prevent vacuum lock and permit said bladder to compensate for medicinal fluid volume changes without pre-pressurization of said vial with external air introduced by said hypodermic needle.

2. A vacuum break assembly as in claim 1 wherein said ambient air vent communicates with an interior of said bladder so that said bladder expands or unfolds as said medicinal fluid is withdrawn from said vial.

3. A vacuum break assembly as in claim 2 wherein said bladder is retained in said vial by a retaining collar, said bladder is disposed in the interior volume of said vial, and said air vent communicates with the interior of said bag through said stopper.

4. A vacuum break assembly as in claim 3 wherein said needle sheath sleeve portion is oriented to extend down from a center hole of said annular disc into said vial volume, and said air vent comprises a short tube that communicates with a lumen associated with the side wall of said sleeve portion, said sleeve is closed at a bottom end thereof, and said retaining collar is secured to the lower end of said sleeve portion so that said bladder communicates with said lumen, thereby providing a continuous air vent to the exterior of said vial.

5. A vacuum break assembly as in claim 4 wherein said lumen is disposed in the vertical side wall of said sleeve portion.

6. A vacuum break assembly as in claim 3 wherein said needle sheath upper end includes an annular disc to assist in securingly engaging said assembly to said elastomeric stopper.

7. A vacuum break assembly as in claim 1 wherein said bladder is sized to generally conform to the interior volume configuration, said bladder comprises medical grade polymeric material to receive said medicinal fluid on the interior thereof.

8. A vacuum break assembly as in claim 1 wherein said assembly is fitted in the mouth of a neck of a medicinal vial.

9. A vacuum break assembly as in claim 8 wherein said vial fitted with said vacuum break assembly includes a metal cap securing said stopper to said vial neck, and said metal cap includes a plastic flip-off top that tears away a central disk of said cap when removed so that said top surface of said stopper is accessible for penetration into said needle sheath by a hypodermic needle.

10. Medicinal vial assembly for reduction of incidence and propagation of nosocomial infections resulting from airborne pathogen vectors or airborne contaminants introduced into medicinal fluids contained in said vial by pre-pressurization with ambient air injected by a hypodermic needle into said vial in the process of withdrawing a dose aliquot of fluid from the interior of said vial, comprising in operative combination:

a) a vial having a neck, said vial containing an amount of medicinal fluid;

b) an elastomeric stopper configured to fit in said vial neck, said stopper having an exterior surface and an interior surface, and a central web portion defined between said surfaces;

c) a needle sheath secured in association with said stopper, said needle sheath having a sleeve portion projecting into said vial, said sleeve having perforations to permit said medicinal fluid to be accessed by said hypodermic needle when introduced into said vial through said stopper web;

d) a bladder disposed in association with said vial to compensate for change in volume of medicinal fluid in said vial as said medicinal fluid is withdrawn from said vial, said bladder isolating external air for volume compensation from said medicinal fluid so that said vial does not have to be pre-pressurized to prevent vacuum lock; and e) an ambient air vent communicating with said bladder to prevent vacuum lock and permit said bladder to compensate for medicinal fluid volume changes without pre-pressurization of said vial with external air introduced by said hypodermic needle.

11. A medicinal vial as in claim 10 wherein said ambient air vent communicates with an interior of said bladder so that said bladder expands or unfolds as said medicinal fluid is withdrawn from said vial.

12. A vacuum break assembly as in claim 11 wherein said bladder is retained in said vial by a retaining collar, said bladder is disposed in the interior volume of said vial, and said air vent communicates with the interior of said bag through said stopper.

13. A medicinal vial as in claim 12 wherein said vial includes a metal cap securing said stopper to said vial neck, and said metal cap includes a plastic flip-off top that tears away a central disk of said cap when removed so that said top surface of said stopper is accessible for penetration into said needle sheath by a hypodermic needle.

14. A vacuum break assembly as in claim 12 wherein said needle sheath sleeve portion is oriented to extend down from a center hole of said annular disc into said vial volume, and said air vent comprises a short tube that communicates with a lumen associated with the side wall of said sleeve portion, said sleeve is closed at a bottom end thereof, and said retaining collar is secured to the lower end of said sleeve portion so that said bladder communicates with said lumen, thereby providing a continuous air vent to the exterior of said vial.

15. A vacuum break assembly as in claim 14 wherein said lumen is disposed in the vertical side wall of said sleeve portion.

16. A vacuum break assembly as in claim 14 wherein said needle sheath upper end includes an annular disc to assist in securingly engaging said assembly to said elastomeric stopper.

17. A vacuum break assembly as in claim 14 wherein said bladder is sized to generally conform to the interior volume configuration, said bladder comprises medical grade polymeric material to receive said medicinal fluid on the interior thereof.

18. A vacuum break assembly as in claim 14 wherein said vial fitted with said vacuum break assembly includes a metal cap securing said stopper to said vial neck, and said metal cap in-cludes a plastic flip-off top that tears away a central disk of said cap when removed so that said top surface of said stopper is accessible for penetration into said needle sheath by a hypodermic needle.

* * * * *